United States Patent

Böer et al.

[11] 4,241,075
[45] Dec. 23, 1980

[54] ACARICIDAL 1-ALKYLTHIO-SUBSTITUTED AND 1-PHENYLTHIO SUBSTITUTED 2-(PHENOXYALKYL)-2-IMIDAZOLINES

[75] Inventors: Manfred Böer, Weil am Rhein, Fed. Rep. of Germany; Jozef Drabek, Oberwil, Switzerland; Günter Mattern, Liestal, Switzerland; Walter Traber, Reinach, Switzerland

[73] Assignee: Ciba-Geigy Corporation, Ardsley, N.Y.

[21] Appl. No.: 76,107

[22] Filed: Sep. 17, 1979

[30] Foreign Application Priority Data

Sep. 27, 1978 [CH] Switzerland ............... 10086782/78
Apr. 24, 1979 [CH] Switzerland ............... 3836792/79

[51] Int. Cl.³ .................. A01N 43/50; C07D 233/22
[52] U.S. Cl. .......................... 424/273 R; 548/351; 548/353
[58] Field of Search ............... 548/351; 424/273 R

[56] References Cited

FOREIGN PATENT DOCUMENTS 1935479  1/1971  Fed. Rep. of Germany .
2756639 12/1977  Fed. Rep. of Germany .
51106739 9/1976  Japan .

Primary Examiner—John D. Randolph
Assistant Examiner—Richard A. Schwartz
Attorney, Agent, or Firm—John J. Maitner; Prabodh I. Almaula

[57] ABSTRACT

Compounds of the formula I

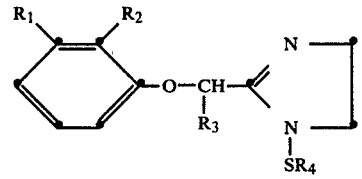

wherein $R_1$ and $R_2$ are each chlorine or methyl, $R_3$ is hydrogen or $C_1$-$C_4$-alkyl and $R_4$ is $C_1$-$C_6$-alkyl optionally substituted by cyano or phenyl optionally substituted by halogen and/or methyl are novel and are pesticidally in particular acaricidally active.

14 Claims, No Drawings

ACARICIDAL 1-ALKYLTHIO-SUBSTITUTED AND 1-PHENYLTHIO SUBSTITUTED 2-(PHENOXYALKYL)-2-IMIDAZOLINES

The present invention relates to novel 1-alkylthio-substituted and 1-phenylthio-substituted 2-(phenoxyalkyl)-2-imidazolines which are effective against pests, a process for their manufacture, acaricidal compositions which contain them as active component, and a method of controlling pests of the order Acarina which comprises the use of the novel compounds.

1-Substituted 2-(phenoxyalkyl)-2-imidazolines having pesticidal, in particular ectoparasiticidal, action are known (cf. Japanese published patent specification 76/106739 and German Offenlegungsschrift No. 2 756 639). The present invention provides novel compounds of this type which also are effective against pests, especially against representatives of the order Acarina, and which are particularly suitable for practical use because of their advantageous biological properties.

The 1-alkylthio-substituted and 1-phenyl-substituted 2-(phenoxyalkyl)-2-imidazolines of the present invention have the formula

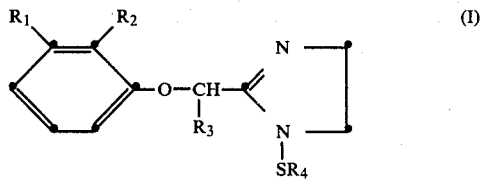

wherein $R_1$ and $R_2$ are each chlorine or methyl, $R_3$ is hydrogen or $C_1$-$C_4$ alkyl, and $R_4$ is $C_1$-$C_6$ alkyl optionally substituted by cyano or is phenyl optionally substituted by halogen and/or methyl.

Alkyl within the definition of $R_3$ and $R_4$ is methyl, ethyl, n-propyl, isopropyl, n-butyl, isobutyl, sec- and tert-butyl, whilst $R_4$ can also be the n-pentyl and n-hexyl group and the isomers thereof. Such alkyl groups also form the alkyl moiety of substituted alkyl groups.

In the compounds of formula I, the following types of substituents and combinations thereof are preferred:
(1) for $R_3$: hydrogen and ethyl, especially ethyl; and
(2) for $R_4$: 2-cyano-prop-2-yl and phenyl which is unsubstituted or mono- or disubstituted by halogen and/or methyl.

The present invention is based on the surprising observation that, compared with the nearest known analogs, namely 1-methylsulfonyl- and 1-phenylsulfonyl-2-(2,3-dimethylphenoxymethyl)-2-imidazoline, the compounds of formula I above have a superior action both against plant-destructive acarids (mites e.g. of the families Tetranychidae, Tarsonemidae, Eriophyidae, Tyroglyphidae and Glycyphagidae) and against acarids (mites and ticks e.g. of the families Ixodidae, Argasidae, Sarcoptidae and Dermanyssidae) which are harmful to productive livestock. Because of these properties, the compounds of formula I are particularly suitable for controlling pests of the order Acarina in ornamentals and crops of cultivated plants as well as for controlling ectoparasitic ticks and mites in productive livestock.

The compounds of formula I are obtained by methods analogous to known ones, for example by reacting a compound of the formula

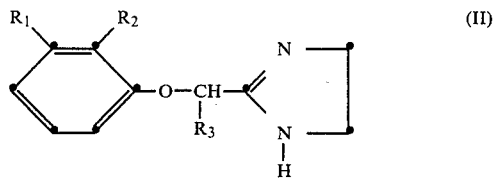

in the presence of a base, with a compound of the formula III

$$X-S-R_4 \quad (III)$$

in which formulae II and III above the symbols $R_1$, $R_2$, $R_3$ and $R_4$ are as defined for formula I and Hal is a halogen atom, in particular a chlorine or bromine atom.

The process is advantageously carried out at a temperature between $-20°$ and $+30°$ C., under normal or slightly elevated pressure, and preferably in the presence of a solvent or diluent which is inert to the reactants.

Examples of suitable solvents or diluents are ethers and ethereal compounds, such as diethyl ether, diisopropyl ether, dioxane and tetrahydrofurane; aromatic hydrocarbons, suh as benzene, toluene and xylenes; ketones, such as acetone, methyl ethyl ketone and cyclohexanone.

Suitable bases for this process are in particular tertiary amines, auch as trialkylamines, pyridines and dialkyl anilines, and hydroxides, oxides, carbonates and bicarbonates of alkali metals and alkaline earth metals, and also alkali metal alcoholates, e.g. potassium tert-butylate and sodium methylate.

The compounds of formula I, wherein $R_3$ is alkyl, exist in the form of optically active isomers. Accordingly, racemic mixtures are obtained if no optically active starting materials are employed in the manufacture of these compounds. Such mixtures of isomers can be separated into the individual isomers, e.g. by chromatographic separating methods. The invention is to be construed as comprising both the individual optically active isomers and mixtures thereof.

The starting materials employed in the above process are known (cf. German Offenlegungsschrift No. 2 756 638) or they can be obtained by methods analogous to known ones.

The compounds of formula I are employed in this invention as pure active substance or they form a constituent of compositions which additionally contain suitable carriers or adjuvants or mixtures thereof.

Suitable carriers and adjuvants can be solid or liquid and correspond to the substances conventionally used in the art of formulation, e.g. natural or regenerated substances, solvents, dispersing agents, wetting agents, tackifiers, thickeners, binders and/or fertilisers.

The acaricidal action of the compositions of the invention can be substantially broadened by addition of other acaricides and/or insecticides. Examples of suitable additives are: organophosphorus compounds, nitrophenols and derivatives thereof, formamidines, ureas, pyrethroids, carbamates, and chlorinated hydrocarbons.

The compositions of the invention can be formulated e.g. as dusts, granulates, dispersions, solutions and suspensions, and also as water-dispersible wettable powders, pastes, emulsions and emulsifiable concentrates. The content of active substance (compound of formula I) in the above compositions is between 0.1 and 95%, though higher concentrations can also be used if the compositions are applied from an aircraft or other appropriate application device.

The active substances of the formula I can be formulated e.g. as follows (throughout this specification, the parts are by weight):

EMULSIFIABLE CONCENTRATE I 20 parts of active substance of the formula I are dissolved in 70 parts of xylene, and to this solution are added 10 parts of an emulsifying agent consisting of a mixture of an arylphenylpolyglycol ether and the calcium salt of dodecylbenzenesulfonic acid. The resultant emulsifiable concentrate can be diluted with water in any ratio to form a milky emulsion.

EMULSIFIABLE CONCENTRATE II

With stirring, 5 to at most 30 parts of active substance are dissolved at room temperature in 30 parts of dibutyl phthalate, 10 parts of Solvent 200 (low viscosity, highly aromatic petroleum distillate) and 15 to 35 parts of Dutrex 238 FC (viscous highly aromatic petroleum distillate). To this solution are added 10 parts of an emulsifier mixture consisting of castor oil polyglycol ether and the calcium salt of dodecylbenzenesulfonate. The resultant emulsifiable concentrate forms milky emulsions in water.

WETTABLE POWDER

The following ingredients are intensively mixed in a mixing apparatus: 5 to 30 parts of active substance, 5 parts of an absorbent carrier (silica gel K 320 or Wessalon S), 55 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5–15 μm in a disc attrition mill or air jet mill. The resultant wettable powder forms a good suspension in water.

DUST 5 parts of finely ground of active substance are intensively mixed with 2 parts of precipitated silicic acid and 93 parts of talcum.

POUR-ON SOLUTION

A 100 ml pour-on solution is obtained as follows: With stirring, 30.0 g of active substance are dissolved in 48.0 g of benzyl alcohol, if necessary while heating gently. Then 3.0 g of sodium dioctylsulfosuccinate and 19.8 g of ground nut oil are added to the above solution and dissolved by heating and thorough stirring.

The invention is illustrated in more detail by the following Examples.

EXAMPLE 1

Manufacture of 1-(2-cyano-prop-2-ylthio)-2-[1-(2,3-dimethylphenoxy)-propyl]-2-imidazoline With continuous stirring and cooling, 4.1 g of α-(chlorothio)-isobutyronitrile are added dropwise at 0° to 10° C. to a solution of 6.97 g of 2-[1-(2,3-dimethylphenoxy)-propyl]-2-imidazoline of the formula

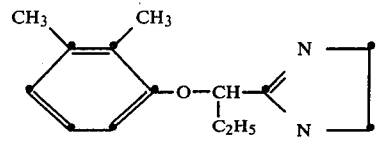

and 4 g of triethylamine in 80 ml of toluene. The reaction mixture is stirred for 1 hour at room temperature, then the toluene phase is washed repeatedly with water and dried. The toluene is then evaporated off, affording 1-(2-cyano-prop-2-ylthio)-2-[1-(2,3-dimethylphenoxy)-propyl]-2-imidazoline of the formula

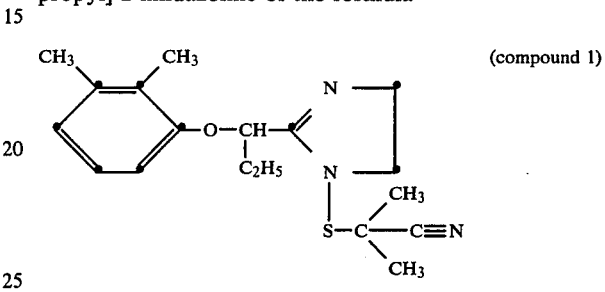

(compound 1)

in the form of a yellow viscous oil with a melting point of 58°–60° C. The following compounds of the formula I can be obtained by procedures analogous to the one described in this Example:

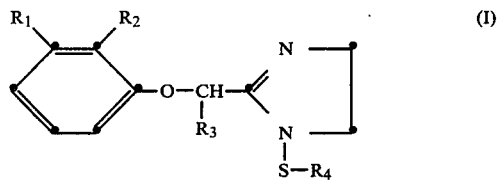

| Compound | $R_1$ | $R_2$ | $R_3$ | $R_4$ | Physical data |
|---|---|---|---|---|---|
| 2 | $CH_3$ | $CH_3$ | $C_2H_5$ | $CH_3$ | |
| 3 | $CH_3$ | $CH_3$ | H | $-C(CH_3)_2-CN$ | m.p. 77°–79° C. |
| 4 | Cl | $CH_3$ | $CH_3$ | $-C(CH_3)_2-CN$ | $n_D^{20}$: 1.5554 |
| 5 | $CH_3$ | $CH_3$ | $n-C_4H_9$ | $-C(CH_3)_2-CN$ | |
| 6 | $CH_3$ | $CH_3$ | $C_2H_5$ | $n-C_6H_{13}$ | |
| 7 | $CH_3$ | $CH_3$ | H | phenyl | m.p. 61°–63° C. |
| 8 | $CH_3$ | $CH_3$ | $n-C_3H_7$ | $-C(CH_3)_2-CN$ | $n_D^{20}$: 1.5403 |
| 9 | $CH_3$ | $CH_3$ | H | 4-Cl-phenyl | m.p. 79°–90° C. |
| 10 | $CH_3$ | $CH_3$ | $C_2H_5$ | 4-Cl-phenyl | $n_D^{20}$: 1.5939 |

-continued

| Compound | R₁ | R₂ | R₃ | R₄ | Physical data |
|---|---|---|---|---|---|
| 11 | CH₃ | CH₃ | H | (furan-CH₃) | m.p. 79°–81° C. |
| 12 | CH₃ | CH₃ | C₂H₅ | (furan-CH₃) | $n_D^{20}$: 1.5838 |
| 13 | Cl | Cl | C₂H₅ | (furan-CH₃) | $n_D^{20}$: 1.6035 |
| 14 | CH₃ | CH₃ | C₂H₅ | CH₃-(furan)-CH₃ | m.p. 67°–69° C. |
| 15 | CH₃ | CH₃ | H | CH₃-(furan)-CH₃ | $n_D^{20}$: 1.5818 |

EXAMPLE 2

Action against plant-destructive acarids (mites) *Tetranychus urticae* (OP-sensitive) and *Tetranychus cinnabarius* (OP-tolerant)

The primary leaves of Phaseolus vulgaris plants were infected with a infested piece of leaf from a mass culture of *Tetranychus urticae* (OP-sensitive) or *Tetranychus cinnabarius* (OP-tolerant). (The tolerance refers to the tolerance to diazinone). The treated, infested plants were sprayed dripping wet with a test solution containing 400 or 200 ppm of the compound to be tested. The number of living and dead imagines and larvae (all mobile stages) was evaluated under a stereoscopic microscope after 24 hours and again after 7 days. One plant was used for each test substance and test species. During the test run, the plants stood in greenhouse compartments at 25° C.

In the above test, the compounds of formula I were effective against adults and larvae of the species *Tetranychus urticae* and *Tetranychus cinnabarius*.

EXAMPLE 3

Action against ectoparasitic acarids (ticks: *Rhipicephalus bursa* (imagines and larvae), *Amblyomma hebraeum* (♀ imagines, nymphs and larvae) and *Boophilus microplus* (larvae, OP-sensitive and OP-tolerant)

The test organisms employed were about 50 larvae, about 25 nymphs or about 10 imagines of each of the tick species *Rhipicephalus bursa, Amblyomma hebraeum* and *Boophilus microplus*. The test organisms were immersed briefly in an aqueous emulsion or solution containing 0.1, 1.0, 10, 50 or 100 ppm of the respective compound. The emulsions or solutions in test tubes were then absorbed by cotton wool and the wetted test organisms were kept in the contaminated tubes. Evaluation of mortality at each concentration was made after 3 days (larvae) and 14 days (nymphs and imagines).

Compounds of the formula I were effective in this test against larvae, nymphs and imagines of *Rhipicephalus bursa* and *Amblyomma hebraeum* and against larvae (OP-resistant and OP-sensitive) of *Boophilus microplus*.

What is claimed is:

1. A compound of the formula I

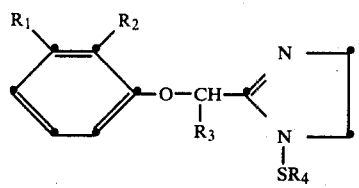

wherein R₁ and R₂ are each chlorine or methyl, R₃ is hydrogen or C₁–C₄-alkyl and R₄ is C₁–C₆-alkyl optionally mono-substituted by cyano or is phenyl optionally mono- or di-substituted by halogen and/or methyl.

2. A compound as claimed in claim 1 wherein R₃ is hydrogen or ethyl.

3. A compound as claimed in claim 2 wherein R₃ is ethyl.

4. A compound as claimed in claims 1, 2 or 3 wherein R₄ is 2-cyan-prop-2-yl or phenyl optionally mono- or di-substituted by halogen or methyl.

5. The compound as claimed in claim 3 of the formula

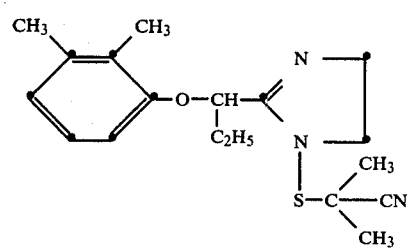

6. The compound as claimed in claim 3 of the formula

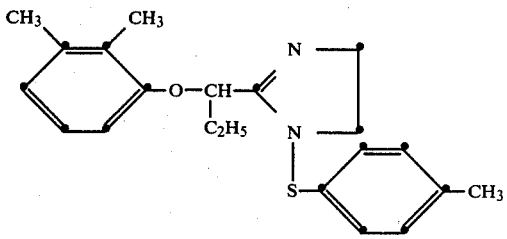

7. An acaricidal composition comprising an acaricidally effective amount of a compound of the formula I as defined in claim 1 together with an inert diluent or carrier therefor.

8. A method of controlling pests of the order Acarina at a locus, which method comprises applying to said locus an acaricidally effective amount of a compound of the formula I as defined in claim 1.

9. A method according to claim 8 in which, in the compound, R₃ is hydrogen or ethyl.

10. A method according to claim 9 in which R₃ is ethyl.

11. A method according to claims 9, 10 or 11 in which, in the compound, R₄ is 2-cyan-prop-2-yl or phenyl optionally mono- or di-substituted by halogen or methyl.

12. The compound as claimed in claim 3 of the formula

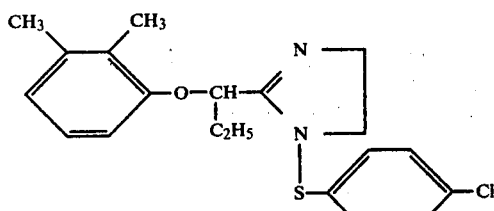
13. The compound as claimed in claim 3 of the formula
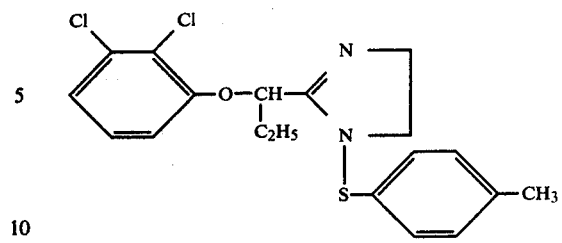
14. The compound as claimed in claim 3 of the formula
* * * * *